United States Patent [19]

Wagaman et al.

[11] 4,400,562
[45] Aug. 23, 1983

[54] ALKENOL SYNTHESIS

[75] Inventors: Kerry L. Wagaman, Waldorf; Larry D. Henderson, Byrans Road, both of Md.

[73] Assignee: The United States of America as represented by the Secretary of the Navy, Washington, D.C.

[21] Appl. No.: 279,645

[22] Filed: Jul. 2, 1981

[51] Int. Cl.$^3$ .................. C07C 29/60; C07C 77/02
[52] U.S. Cl. .................................. 568/903; 260/467
[58] Field of Search ........................................ 568/903

[56] References Cited

U.S. PATENT DOCUMENTS 2,422,802 6/1947 Schelling et al. ............... 568/903
3,001,975 9/1961 Beavers et al. .................. 568/903
3,636,167 1/1972 Tedeschi et al. ................. 568/903

FOREIGN PATENT DOCUMENTS 950634 10/1956 Fed. Rep. of Germany ...... 568/903

OTHER PUBLICATIONS

Traynelis et al., *J. Org. Chem.* 27, pp. 123–128 (1962).
Malcolm E. Winfield, *J. Council Sci. Ind. Res.* 18, pp. 412–423 (1945).

*Primary Examiner*—J. E. Evans

[57] ABSTRACT

3-Buten-1-ol is synthesized from 1,3-butanediol by heating a polyol in the presence of a trivalent metal sulfate to a temperature from about 70° C. below to about 100° C. above the boiling point of 1,3-butanediol.

5 Claims, No Drawings

ND SYNTHESIS

ALKENOL SYNTHESIS

BACKGROUND OF THE INVENTION

The invention pertains generally to organic synthesis and in particular to a controlled method of partially dehydrating a polyol to form an unsaturated alcohol.

Nitrate esters of polyols are used extensively as explosives and as energetic plasticizers for nitrocellulose in propellants. The most commonly used nitrate ester is nitroglycerin, but it has a number of problems. The nitrate ester of 1,2,4-butanetriol has a lower volatility and sensitivity, and is a better plasticizer. It is, unfortunately, much more expensive than nitroglycerin.

It is known that this triol can be easily and cheaply prepared from 3-buten-1-ol, but the unsaturated alcohol is difficult to prepare. Every known method for preparing this alcohol has disadvantages which increase the cost of the final product. A laboratory procedure, reported in J. A. Gallaghan et al, *Technical Report* 19, Naval Powder Factory, Indian Head, Md. (1948), converts allyl chloride by means of a Barber modification of a Grignard reaction. The yields from this method are high (up to 65%), but attempts at scaling-up this method to production have been unsuccessful.

Attempts at dehydrating butanediol to 3-buten-1-ol have had many problems. Most reactions proceed until the diol has been completely dehydrated to butadiene. The dehydrations which are controllable produce numerous side reactions, causing the product yield to be low. Usually the dehydrations proceed in the gas phase which greatly increases the equipment and energy costs and presents problems in maintaining a uniform temperature throughout the reactor. Many of the catalysts have a short life, are expensive, and are expensive to regenerate.

SUMMARY OF THE INVENTION

It is, therefore, an object of the present invention to prepare inexpensively and quickly, unsaturated alcohols, in particular 3-buten-1-ol, from polyhydric alcohols.

Another object of the present invention is to prepare unsaturated alcohols by a method involving few side reactions.

And another object of the present invention is to produce unsaturated alcohols in high yields and with few impurities.

A further object of the present invention is to prepare unsaturated alcohols from polyhydric alcohols in the liquid phase, thereby reducing equipment and energy costs.

These and other objects are achieved by heating a polyol in the presence of a trivalent metal sulfate to a temperature from about 70° C. below to about 100° C. above the boiling point of the polyol.

DETAILED DESCRIPTION OF THE INVENTION

The catalysts found to be effective in partially dehydrating polyols to form unsaturated alcohols are trivalent metal sulfates. The preferred catalysts are aluminum, ferric, and chromium sulfate and mixtures thereof.

A wide range of aliphatic polyols can be dehydrated, so long as hydroxyl groups are are not on both ends of the carbon chain and the number of carbon atoms is from 3 to 8. However, the importance of the present invention derives from the partial dehydration of alkane diols to alkenols. Of particular importance is the partial dehydration of 1,3-butanediol to 3-buten-1-ol in a high yield with minor amounts of 2-buten-1-ol, 3-buten-2-ol, 2-buten-2-ol, ketones, and olefins.

The dehydration of the polyols can be done neat or with a liquid inert miscible diluent for the polyol. The preferred diluents are aliphatic hydrocarbons which have a boiling point at least equal to about the boiling point of the desired alkenol. Examples of preferred diluents for butanediol are dodecane and octadecane. In reacting the polyol neat, the amount of polyol present must be sufficient to keep the catalyst in suspension by agitation. Otherwise a portion of the catalyst settles out and the moist catalyst completely dehydrates the polyol to a diene compound. If a diluent is used, then the amount of diluent should be such that the entire amount of catalyst can be suspended.

The temperature at which the dehydration is carried out is from about 70° C. below to about 100° C. above the boiling point of the polyol and preferably from 30° C. below to about 50° C. above the boiling point of the polyol. If the temperature is too high, the polyol boils before dehydrating and if the temperature is too low, dehydration does not occur or occurs too slowly to be practical. For butanediol, the preferred reaction temperature is from 177° C. to 257° C. and most preferably from 190° to 225° C. The type and degree of agitation are not critical so long as the catalyst remains suspended.

The order of addition is not critical; however, if the polyol is added to a heated catalyst, the polyol should be added slowly to avoid splattering. One preferred method is to form a suspension of the catalyst in one of the above diluents, heat the suspension, and add the polyol to the suspension. In order to avoid cold spots in the reactor, it is preferred that the polyol is heated above room temperature, generally from 100° C. below to about 10° C. below the boiling point of the polyol. Another preferred method is to form a suspension of the catalyst in the polyol or in the polyol and diluent, heat the reaction fluid to the desired temperature, and add polyol as the polyol in the reactor is dehydrated. Preferably the polyol is added at a rate which avoids spattering and within the above temperature range to avoid creating cold spots in the reaction fluid. The catalyst should remain wet; otherwise, the polyol would come into contact with dry catalyst and be additionally dehydrated to a diene, thus creating a possible safety hazard.

In a plug flow reactor whereby a stream of polyol neat or diluted passes through a fixed bed of catalyst, then the flow must be rapid in order to present the double dehydration to butadiene.

The gaseous products are preferably collected by condensation and the alkenol is preferably separated by fractional distillation. With the present method, the purity of the product after fractional distillation is sufficient for most uses, e.g., synthesis of alkane triols.

The invention having been generally described, the following examples are given to illustrate the practice and advantages of the present invention. It is understood that the examples are given by way of illustration and are not meant to limit the specification or the claims to follow in any manner.

The reactor was a four-necked flask fitted with a thermometer, a feed line, an agitator, and a distillation column with a condenser. The condensate was analyzed by Perkin-Elmer gas chromatograph.

Table I summarizes the reaction conditions of a batch example (I) and four continuous examples (II-V). Table II summarizes the analysis of the condensate. The temperature of reactions 2, 3, and 4 was varied. The percentages are of the condensate with the remainder of the condensate being water and minor amounts of organic by-products.

TABLE I

| Reaction Number | Catalyst Type | Catalyst Weight | Inert Diluent | To Catalyst Butadediol Wt Ratio | Reaction Temperature |
|---|---|---|---|---|---|
| 1 | $Fe_2(SO_2)_3 \cdot XH_2O$ | 50g | 200mls dodecane | 2:1 | 200° C. |
| 2a | $Fe_2(SO_4)_2 \cdot XH_2O$ | 100g | — | 10:1 | 140° C. |
| b | | | | | 150° C. |
| c | | | | | 169° C. |
| d | | | | | 180° C. |
| e | | | | | 196° C. |
| f | | | | | 204° C. |
| 3a | $Fe_2(SO_4)_3 \cdot XH_2O$ | 500g | — | 2:1 | 104° C. |
| b | | | | | 159° C. |
| 4a | $Al_2(SO_4)_3 \cdot XH_2O$ | 100g | — | 10:1 | 163° C. |
| b | | | | | 186° C. |
| c | | | | | 213° C. |
| 5 | $Cr_2(SO_4)_3 \cdot XH_2O$ | 500g | — | 3:1 | 182° C. |

TABLE II

| Reaction Number | %3-Buten-2-ol | %3-Buten-1-ol | %1,3-Butanediol |
|---|---|---|---|
| 1 | 6 | 36 | — |
| 2a | 4.7 | 24.4 | 5 |
| b | 2.6 | 13.8 | 3 |
| c | 1.8 | 13 | 3 |
| d | 1.2 | 15.9 | 13 |
| e | 2.0 | 11.3 | 8 |
| f | 1.8 | 14.2 | 21 |
| 3a | 2.5 | 11.4 | 2 |
| b | 1.5 | 12.2 | — |
| 4a | 3.3 | 16.0 | 55 |
| b | 2.1 | 12.6 | 15 |
| c | 1.9 | 11.5 | 12 |
| 5 | 2.6 | 33 | — |

The results show that the subject invention is able to produce a partial dehydration at a specific point on the carbon chain. No appreciable butadiene was detected, whereas, other salts produced large amounts of butadiene. Thus the subject invention produces a product requiring little purification and presents little hazard.

The catalyst was used continuously for six hours on the above examples and many other runs. No degradation of the catalyst activity was noticed after each of these runs.

An important advantage shown by the experimental data is that the condensate concentration of the undesired 3-buten-1-ol decreases with an increase in temperature. A least-squares plot of the data shows that the ratio of the desired 3-buten-1-ol to the desired 3-buten-2-ol increases from about 5:1 at about 140° C. to about 8:1 at 220° C. Thus a higher rate of reaction, caused by the higher temperature, gives a better product.

Obviously many modifications and variations of this invention are possible to light of the above teachings. It is, therefore, to be understood that within the scope of the appended claims the invention may be practiced otherwise than as specifically described.

What is claimed is:

1. A method for synthesizing an alkenol from 1,3 butanediol in the liquid phase which comprises:
   admixing a trivalent metal sulfate selected from the group consisting of aluminum sulfate, chromium sulfate, ferric sulfate, and mixtures thereof, as a catalyst, with 1,3-butanediol, in an effective amount, thereby forming a mixture of said catalyst suspended in 1,3-butanediol;
   heating said mixture to a temperature from about 70° C. below to about 100° C. above the boiling point of 1,3-butanediol, thereby partially dehydrating 1,3-butanediol to 3-buten-1-ol which flash-evaporates to a vapor; and
   condensing said vapor to isolate 3-buten-1-ol.

2. The method of claim 1 wherein said temperature is from 190° to 225° C.

3. The method of claim 2 wherein an inert diluent having a boiling point higher than 3-buten-1-ol is admixed with said catalyst and 3-buten-1-ol.

4. A method for synthesizing an alkenol from 1,3 butanediol in the liquid phase which comprises:
   admixing an effective amount of a trivalent metal sulfate selected from the group consisting of aluminum sulfate, ferric sulfate, chromium sulfate, and mixtures thereof, as a catalyst, with an inert diluent having a boiling point higher than 3-buten-1-ol, thereby forming a mixture of said catalyst suspended in said diluent;
   heating said mixture to a temperature from about 70° C. below to about 100° C. above the boiling point of 1,3-butanediol;
   adding slowly 1,3-butanediol to said mixture, thereby partially dehydrating 1,3-butanediol to 3-buten-1-ol which flash-evaporates to a vapor; and
   condensing said vapor to isolate 3-buten-1-ol.

5. The method of claim 4 wherein said temperature is from 190° to 225° C.

* * * * *